United States Patent
Bregulla et al.

(10) Patent No.: US 10,646,362 B2
(45) Date of Patent: May 12, 2020

(54) DOUBLE STENT

(71) Applicant: Bentley InnoMed GmbH, Hechingen (DE)

(72) Inventors: Rainer Bregulla, Balingen (DE); Milisav Obradovic, Lorrach (DE)

(73) Assignee: Bentley InnoMed GmbH, Hechingen (DE)

( * ) Notice: Subject to any disclaimer, the term of this patent is extended or adjusted under 35 U.S.C. 154(b) by 134 days.

(21) Appl. No.: 16/062,447

(22) PCT Filed: Jan. 12, 2017

(86) PCT No.: PCT/EP2017/050574
§ 371 (c)(1),
(2) Date: Jun. 14, 2018

(87) PCT Pub. No.: WO2017/125312
PCT Pub. Date: Jul. 27, 2017

(65) Prior Publication Data
US 2018/0360631 A1 Dec. 20, 2018

(30) Foreign Application Priority Data
Jan. 19, 2016 (DE) .................. 10 2016 100 774

(51) Int. Cl.
*A61F 2/915* (2013.01)
*A61F 2/07* (2013.01)
*A61F 2/852* (2013.01)

(52) U.S. Cl.
CPC ............. *A61F 2/915* (2013.01); *A61F 2/07* (2013.01); *A61F 2/852* (2013.01); *A61F 2002/075* (2013.01); *A61F 2002/91516* (2013.01); *A61F 2002/91575* (2013.01)

(58) Field of Classification Search
CPC .. A61F 2/915; A61F 2/852; A61F 2/07; A61F 2002/91516; A61F 2002/91575; A61F 2002/075
USPC ..... 623/1.11, 1.13, 1.15; 606/191, 192, 194, 606/195, 198
See application file for complete search history.

(56) References Cited

U.S. PATENT DOCUMENTS

| | | | | |
|---|---|---|---|---|
| 5,667,523 A | * | 9/1997 | Bynon | A61F 2/07 606/194 |
| 5,693,085 A | * | 12/1997 | Buirge | A61F 2/0022 606/192 |
| 6,124,523 A | * | 9/2000 | Banas | A61F 2/07 606/191 |

FOREIGN PATENT DOCUMENTS

| | | |
|---|---|---|
| DE | 296 23 983 U1 | 12/2000 |
| EP | 0 878 173 A1 | 11/1998 |
| WO | WO 2012/084202 A2 | 6/2012 |

OTHER PUBLICATIONS

Written Opinion dated Aug. 2, 2018 in connection with PCT/EP2017/050574 filed Jan. 12, 2017.

\* cited by examiner

*Primary Examiner* — Vy Q Bui
(74) *Attorney, Agent, or Firm* — Brooks Kushman P.C.

(57) ABSTRACT

The invention relates to a double stent comprising 2 coaxially arranged stents, wherein a first membrane is arranged between a first inner stent and a second outer stent and a second membrane is arranged on the second stent and wherein the membrane ends of the first and second membrane are brought together at the ends of the stents and are folded over onto the inside of the first stent and clamped under flexible tongues of the first stent.

12 Claims, 2 Drawing Sheets

DOUBLE STENT

The invention relates to a double stent comprising 2 coaxially arranged stents, whereby a first membrane is arranged between a first inner stent and a second outer stent. The double stent is used in particular as a stent graft for the purpose of bridging vascular malformations, such as aneurysms and shunts, but also to reinforce unstable, fragile or thrombotic vessel walls. It is, moreover, applied as a bridge for branches from stented vessels.

Stent grafts for bridging vascular malformations are known in a variety of forms. As a rule, they consist of a stent that is completely or partially covered with a membrane. The membrane occludes the vascular malformation against the vessel, the stent keeps the vessel open and ensures that the membrane is in close contact with the vessel wall.

One problem with stent grafts is the anchoring of the membrane to the stent. Double stents were developed for this purpose, in which the membrane is held between an outer and an inner stent. During the expansion of such a double stent, the membrane participates in the radial expansion but remains clamped between the two stents.

Such a double stent is known, for example, from what has been disclosed in DE 197 20 115 A1. The stent described there has proven its worth in and of itself but can be improved in two respects.

On the one hand, problems with tightness are often encountered, as the membrane is not in close contact with the vessel wall and/or is damaged during the expansion of the double stent. In both cases, the double stent does not meet the requirements placed on it, namely the occlusion of, for example, a vascular malformation.

On the other hand, the expansion of the double stent may cause the composite of two stents and a membrane to lose coherence, for example if the two stents exhibit a different expansion behavior—for example due to local conditions.

When normal stent grafts are used, the radial force of a single stent, whether of balloon expandable or self-expanding type, is not sufficient in many cases to securely anchor the membrane and/or ensure a reliable and permanent bridging or expansion of the vessel. In these cases, the use of a double stent with increased radial force is considered to be expedient. This applies in particular to self-expanding stents, which generally have a lower radial force than balloon-expandable stents.

It is, therefore, the objective of the invention to provide a double stent that meets the requirements with respect to tightness and reliability on the one hand and, moreover, warrants the required coherence on the other. In addition, the stent should have a high radial force.

This objective is achieved with a double stent of the kind first mentioned above, in which a second membrane is arranged on the second outer stent, wherein the membrane ends of the first and second membrane being brought together at the ends of the stents, folded over to the inside of the first stent and clamped under flexible tongues of the first stent.

The double stent proposed by the invention not only comprises an inner and an outer stent but is also provided with an inner and outer membrane. What is more, the two stents complement each other in terms of radial force and the two diaphragms in terms of tightness. The outer second membrane serves as protection and supplement to the inner first membrane so that, if the inner membrane is damaged during expansion, for example tears, the outer membrane is capable of compensating for this defect and vice versa. Furthermore, the outer membrane holds the construct together, whereby anchoring the ends of the outer membrane—together with the ends of the inner membrane—on the inside of the inner stent contributes to the coherence of the elements.

For the stents used according to the invention, the usual stent designs, such as those often developed for balloon-expandable and self-expanding stents, can be put to use. For balloon-expandable stents any materials customary for this purpose may be employed, for example, steel alloys for medical use, cobalt-chromium alloys and the like. As regards self-expanding stents, materials with shape memory properties are particularly suitable, such as nickel-titanium alloys.

The stents can be braided but are usually cut from a tube of suitable diameter using a laser cutting technique. They feature a mesh structure.

For example, the stents may have a mesh structure as formed by intersecting webs. Stents consisting of a plurality of meandering ring segments are preferred, with said ring segments being connected to adjacent ring segments by means of connecting webs. In this case, too, meshes are produced, the size of which is determined by the frequency of the connecting webs existing between two adjacent ring segments. Such a stent structure is suited to at least partially compensate for the length reduction that occurs during expansion depending on the arrangement and shape of the connecting webs.

The flexible tongues located on the inner first stent can have a variety of shapes. The flexible tongues point into a direction outward of the stent, i.e. they point to the stent edge. Such flexible tongues may, for example, be provided in the form of loops of the ring segments pointing outwards, with the film ends being clamped and secured between the loops and connecting webs originating from the same ring segment.

The inner stent may also have specially designed flexible tongues, for example in the form of blind webs, which are arranged in the loops or on outward pointing loop arches and do not establish connections to adjacent ring segments. Flexible tongues can also be provided in the form of incisions made in the loop arches in such a way that the loop arches are split and securely hold the membrane ends in the manner of a paper clip.

Clamping the membrane ends on the inside of the inner stent results in reliably anchoring and securing the two membranes and strengthens the bond comprising the inner stent, the inner membrane, the outer stent and the outer membrane.

The flexible tongues of the inner stent always point to the outside of the stent. They are as a rule located in the edge zone of the inner stent, preferably at the ring segment arranged adjacent to the peripheral ring segment.

Any biological or artificial material suitable for the purpose can be employed for the membranes. Usually, the membranes consist of plastic material, preferably a plastic tube, which is pulled over the respective stent. For example, a suitable material is polytetrafluoroethylene, PTFE, especially ePTFE, which has the elasticity required for the expansion process. Other plastics unobjectionable from a medical viewpoint, such as polyester, polyolefins, polyurethanes, polyurethane carbonate and the like, may also be employed.

It goes without saying that different designs can be used for the inner and outer stent and the inner and outer membrane can be produced of different materials.

The application of two stents and two membranes naturally leads to a relatively high wall thickness of the construct, which limits maneuverability in a patients vascular system. This can be counteracted by selecting a low wall thickness for the tubes from which the stents are cut, for example in the range of between 0.05 and 0.50 mm, preferably between 0.10 to 0.20 mm and in particular approx. 0.15 mm. The web width as well can be reduced, for example, to between 0.05 and 0.50 mm, preferably between 0.10 and 0.20 mm and in particular approx. 0.15 mm. As a result of two stents being used, a high radial force is still achieved.

It is preferred, moreover, to provide the outer stent with meshes that are smaller than those of the inner stent. In this way, a compressive stress is created during expansion, which has an advantageous effect on the radial force and the coherence of the construct. A high strength and durability of the construct is thus achieved.

The inventive double stent is particularly suitable for placement in branches of stented vessels and thus for bridging the space that forms between the stented vessel and the branch.

Further elucidation of the invention is provided through the enclosed figures showing preferred embodiments of the invention. It goes without saying that the characteristics shown in the figures shall in each case be regarded individually as being part of the invention and should not be understood exclusively in the context of the other characteristics illustrated in the figures, where FIG. 1 is a schematic representation of a stent in accordance with the invention;

Figure 1:
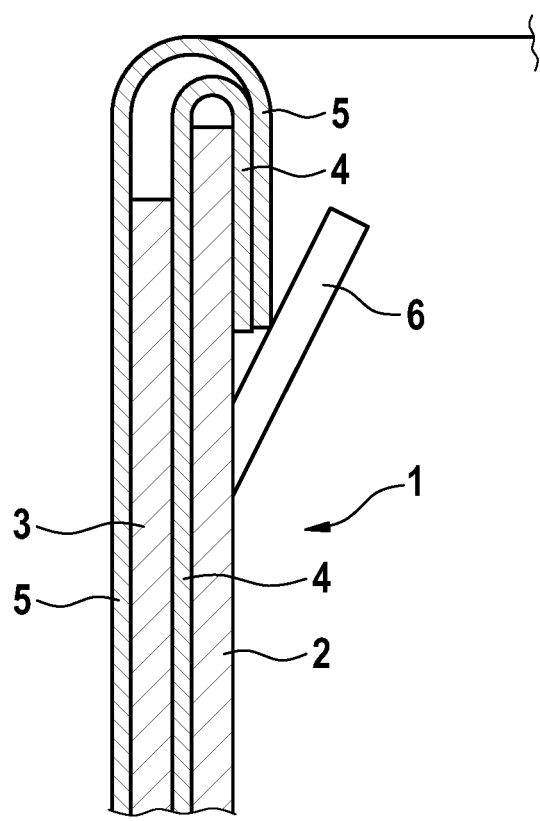

The double stent 1 shown in FIG. 1 comprises a first inner stent 2 and a second outer stent 3 that are arranged coaxially to each other. The outer stent 3 is slightly shorter than the inner stent 2. The double stent is not shown in its expanded state. Between the inner stent 2 and the outer stent 3 a first inner membrane 4 is situated and on the outer stent 3 a second outer membrane 5 is arranged, with both membranes being made of ePTFE.

The inner membrane 4 and the outer membrane 5 are brought together at their ends and folded inwards into the cavity of the inner stent 2 around the edge of the two stents. Schematically shown in the figure is one of several flexible tongues 6, which is bent inwards and under which the membrane ends protrude. For the purpose of fixing the membrane ends, the flexible tongues 6 are bent back outwards resulting in the membrane ends being clamped underneath them.

Figure 2:
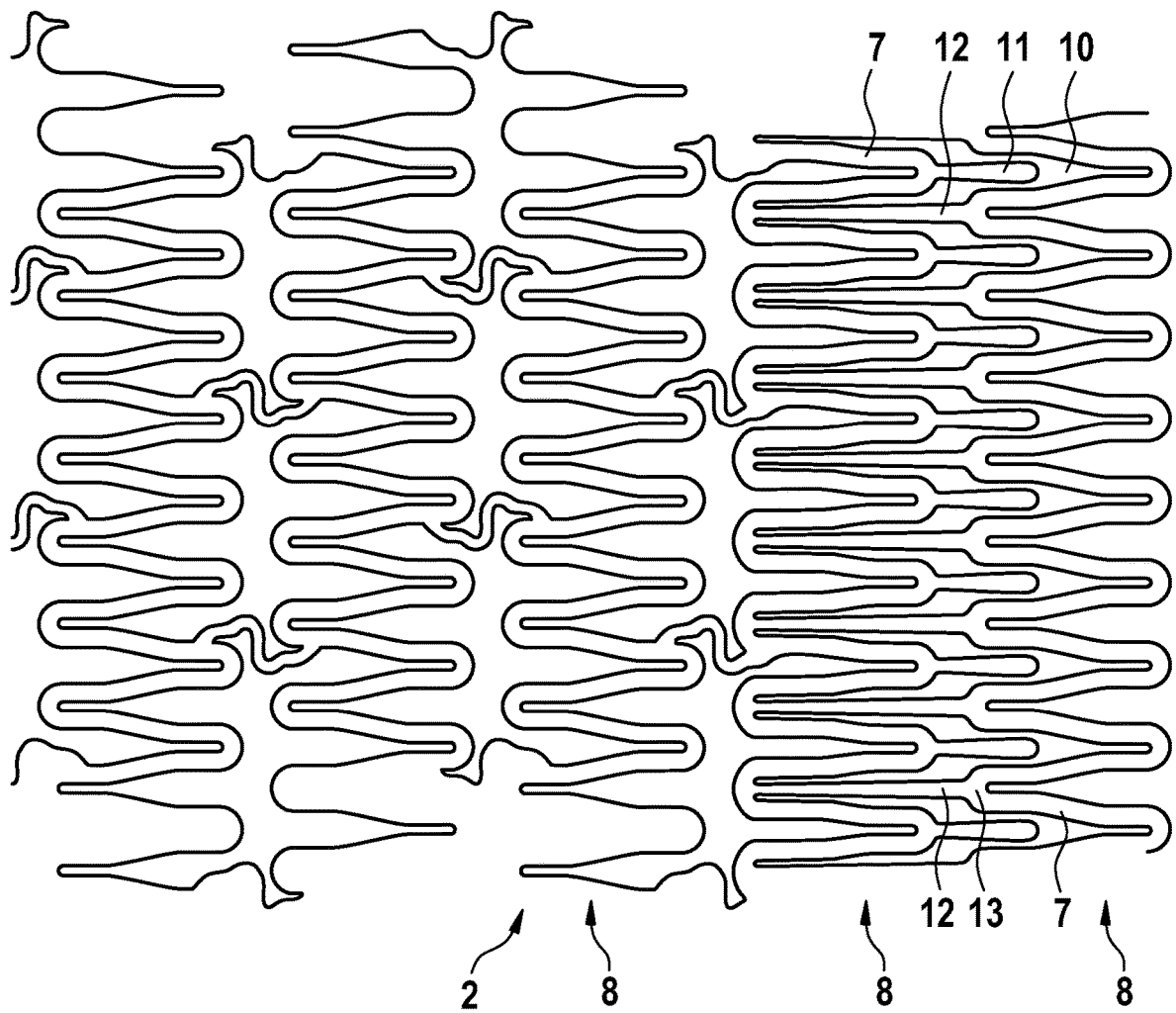
FIG. 2 shows a variant of the clamping principle used for the membranes.

In FIG. 2 a stent design is illustrated for the inner stent 2, in which blind webs 11 project into recesses 10 of a ring segment 8, under which a membrane 4/5 can be pushed so that it is securely held between the loops 7 of the ring segment 8 and the blind webs 11. Adjacent ring segments 8 are joined by means of connecting webs 12, which originate from the reversal points 13.

Figure 3:
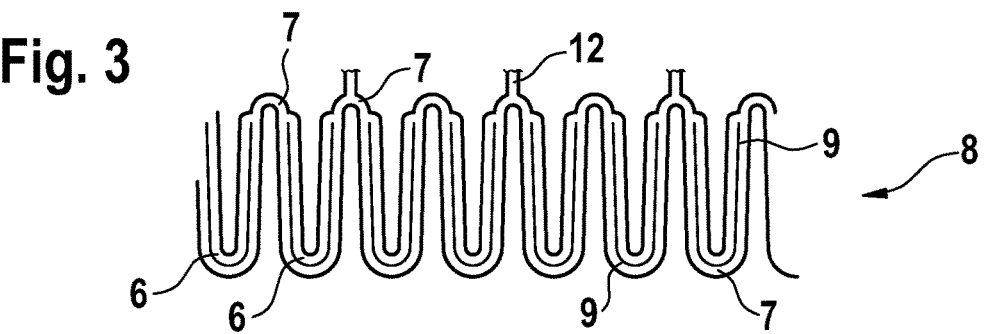
FIG. 3 illustrates another variant of the clamping principle.

FIG. 3 shows a ring segment of a stent design in which the loops 7 of the ring segment 8 have arches 9 cut into them resulting in the flexible tongues 6, which are movable perpendicular to the stent axis, to be able to securely hold a membrane 4/5 pushed underneath in the manner of a paper clip. The stent design forms part of an inner stent 2.

The invention claimed is:

1. Double stent comprising two coaxially arranged stents, wherein a first membrane being arranged between a first inner stent and a second outer stent, characterized in that a second membrane is arranged on the second stent and that the membrane ends of the first and second membrane are brought together at the ends of the stents and are folded over onto the inside of the first stent and clamped under flexible tongues of the first stent.

2. Double stent according to claim 1, characterized in that at least one of the stents has a mesh structure.

3. Double stent according to claim 1, characterized in that at least one of the stents is provided with a plurality of ring segments arranged side by side and having a meandering structure which are connected to one another by webs.

4. Double stent according to claim 1, characterized in that the flexible tongues are blind webs arranged in meshes or loops of the first stent.

5. Double stent according to claim 1, characterized in that the flexible tongues are formed by applying incisions in the web loops of the first stent.

6. Double stent according to claim 1, characterized in that the flexible tongues point to the outside of the stent.

7. Double stent according to claim 1, characterized in that the flexible tongues are arranged in the peripheral regions of the first stent.

8. Double stent according to claim 7, characterized in that the flexible tongues are formed on ring segments arranged adjacent to the peripheral ring segments.

9. Double stent according to claim 1, characterized in that the second stent has a structure that is denser than that of the first stent.

10. Double stent according to claim 1, characterized in that the webs of the first and second stent are arranged with gaps between them.

11. Double stent according to claim 1, characterized in that the first and/or second membrane consists of plastic material.

12. Double stent according to claim 11, characterized in that the first and/or second membrane consists of PTFE.

* * * * *